United States Patent
Hu et al.

(10) Patent No.: US 12,004,908 B2
(45) Date of Patent: Jun. 11, 2024

(54) ULTRASOUND IMAGING SYSTEM FOR HIGH RESOLUTION WIDEBAND HARMONIC IMAGING

(71) Applicant: KONINKLIJKE PHILIPS N.V., Eindhoven (NL)

(72) Inventors: Xiaowen Hu, Bothell, WA (US); Gary Cheng-How Ng, Redmond, WA (US); David Hope Simpson, Bothell, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 427 days.

(21) Appl. No.: 17/050,235

(22) PCT Filed: Apr. 15, 2019

(86) PCT No.: PCT/EP2019/059636
§ 371 (c)(1),
(2) Date: Oct. 23, 2020

(87) PCT Pub. No.: WO2019/206709
PCT Pub. Date: Oct. 31, 2019

(65) Prior Publication Data
US 2021/0077078 A1    Mar. 18, 2021

Related U.S. Application Data

(60) Provisional application No. 62/661,775, filed on Apr. 24, 2018.

(51) Int. Cl.
*A61B 8/00* (2006.01)
*A61B 8/08* (2006.01)
(Continued)

(52) U.S. Cl.
CPC ............ *A61B 8/5269* (2013.01); *A61B 8/145* (2013.01); *A61B 8/4444* (2013.01);
(Continued)

(58) Field of Classification Search
CPC ..... A61B 8/5269; A61B 8/145; A61B 8/4444; A61B 8/4488; A61B 8/5207;
(Continued)

(56) References Cited

U.S. PATENT DOCUMENTS

| 5,879,303 A | 3/1999 | Averkiou et al. |
| 2004/0015079 A1* | 1/2004 | Berger ................. G01S 7/5208 600/443 |
| 2016/0166237 A1* | 6/2016 | Yoshiara ............. G01S 15/8963 600/443 |

FOREIGN PATENT DOCUMENTS

| EP | 1126287 A2 | 8/2001 |
| WO | 0229433 A2 | 4/2002 |

OTHER PUBLICATIONS

International Search Report and Written Opinion for International Application No. PCT/EP2019/059636, filed Apr. 15, 2019, 15 pages.

* cited by examiner

*Primary Examiner* — Serkan Akar
*Assistant Examiner* — Gabriel Victor Popescu (57) ABSTRACT

An ultrasound imaging system transmits two beams in succession in the same beam direction, the waveform of the second beam being a phase inverted form of the first waveform, and each waveform containing first and second major frequency components. Echoes are received from along the beam direction in response to each beam transmission, and are processed by additively and subtractively combining the two echo sequences on a common depth basis. The echo components resulting from this processing
(Continued)

extend from high frequencies for good near field resolution to low frequencies for good depth penetration, and include fundamental, harmonic, and sum or difference frequency components. The linear and nonlinear echo signal components may be frequency compounded for speckle reduction.

14 Claims, 6 Drawing Sheets (51) Int. Cl.
*A61B 8/14* (2006.01)
*G01S 7/52* (2006.01)
*G01S 15/89* (2006.01)

(52) U.S. Cl.
CPC .......... *A61B 8/4488* (2013.01); *A61B 8/5207* (2013.01); *A61B 8/5246* (2013.01); *A61B 8/54* (2013.01); *G01S 7/5202* (2013.01); *G01S 7/52026* (2013.01); *G01S 15/8952* (2013.01); *G01S 15/8963* (2013.01)

(58) Field of Classification Search
CPC ....... A61B 8/5246; A61B 8/54; G01S 7/5202; G01S 7/52026; G01S 15/8952; G01S 15/8963; G01S 7/52038; G01S 7/52047; G01S 7/52077
See application file for complete search history.

ULTRASOUND IMAGING SYSTEM FOR HIGH RESOLUTION WIDEBAND HARMONIC IMAGING

RELATED APPLICATIONS

This application is the U.S. National Phase application under 35 U.S.C. § 371 of International Application No. PCT/EP2019/059636, filed on Apr. 15, 2019, which claims the benefit and priority of Provisional Application No. 62/661,775, filed Apr. 24, 2018. These applications are hereby incorporated by reference herein, for all purposes.

This invention relates to medical ultrasound imaging systems and, in particular, to ultrasound systems which perform high resolution, wideband harmonic imaging.

Harmonic imaging presently finds two major applications in ultrasound imaging. One is the imaging of ultrasonic contrast agents. The microbubbles of contrast agents can be designed to oscillate or break up when insonified by ultrasound. This oscillation or destruction will cause the echoes returned from the microbubbles to be rich in harmonic frequency components. The received echoes are filtered to separate the harmonic components from the fundamental frequency components. A preferred separation technique is known as pulse inversion as described in U.S. Pat. No. 5,951,478 (Hwang et al.) Images produced with these echoes can sharply segment the blood flow and vasculature containing the contrast agent.

The second significant application of harmonic imaging is tissue harmonic imaging in which a generally sinusoidal transmit waveform is allowed to undergo natural distortion as it passes through the body. The distortion gives rise to the development of harmonic frequency components of which the most significant is usually at the second harmonic of the fundamental transmit frequency. The echoes are received and processed in a similar manner as tissue harmonic signals to separate the harmonic components returned from the body. Tissue harmonic imaging is described in U.S. Pat. No. 5,879,303 (Averkiou et al.) Images produced from the harmonic components are desirable for their low level of clutter caused by multipath scattering.

U.S. Pat. No. 6,440,075 (Averkiou) describes another ultrasound imaging technique which enhances the production of nonlinear signal components. This is done by transmitting a waveform with two major frequencies. As the waveform passes through tissue or encounters a microbubble, harmonic components of each transmit frequency will be developed as described above. In addition, the two transmit frequency components will intermodulate, thereby developing sum and difference frequency components. Both types of nonlinear signals are received and used to form images which are enhanced by the use of the two nonlinearity mechanisms. This patent gives examples of several ways in which sum and difference frequencies can be formed and located, such as by using the sides of the transducer passband for the major transmit frequencies and the center for difference and harmonic frequency components.

Tissue harmonic imaging has two significant limitations, its ability to image in the very near field and its ability to image in the far field. Since harmonic components of tissue harmonic imaging only begin to develop after passage of the transmit waves through tissue, there is little or no energy present in the very near field for return of harmonic echoes. For imaging at greater depths in the body, which is often necessary for deep abdominal imaging such as imaging the liver, lower frequencies are required to counter the effects of depth-dependent frequency attenuation. Since second harmonic frequencies are by definition twice the fundamental transmit frequency, they are by nature high frequencies and thus more greatly affected by depth-dependent attenuation. This attenuation can reduce the signal-to-noise characteristic of the received echoes and hence the diagnostic quality of the images. Furthermore, the harmonic components of an echo signal contain only a small portion of the energy reflected in an echo, further diminishing their signal-to-noise characteristic. It is therefore desirable to be able to perform harmonic imaging in a way which will improve the resolution of the images in both the near and far fields of an image.

In accordance with the principles of the present invention, an ultrasound system is described which performs high resolution harmonic imaging by using a wide bandwidth of echo signals. The transmit waveform is designed to contain two major frequency components. The transmit waveform is transmitted twice, each time with a different transmit modulation. The received echoes from the two transmissions are combined in two ways, by addition and subtraction, to extract a full spectrum of image information. This separates the fundamental, harmonic and the intermodulated components of the two major frequency components. These different components include high frequency intermodulation and/or harmonic components which provide good near field resolution, and strong low frequency fundamental components which provide good resolution in the far field. The content of these different frequency components can be accentuated by use of a tracking filter following signal component separation.

Figure 1:
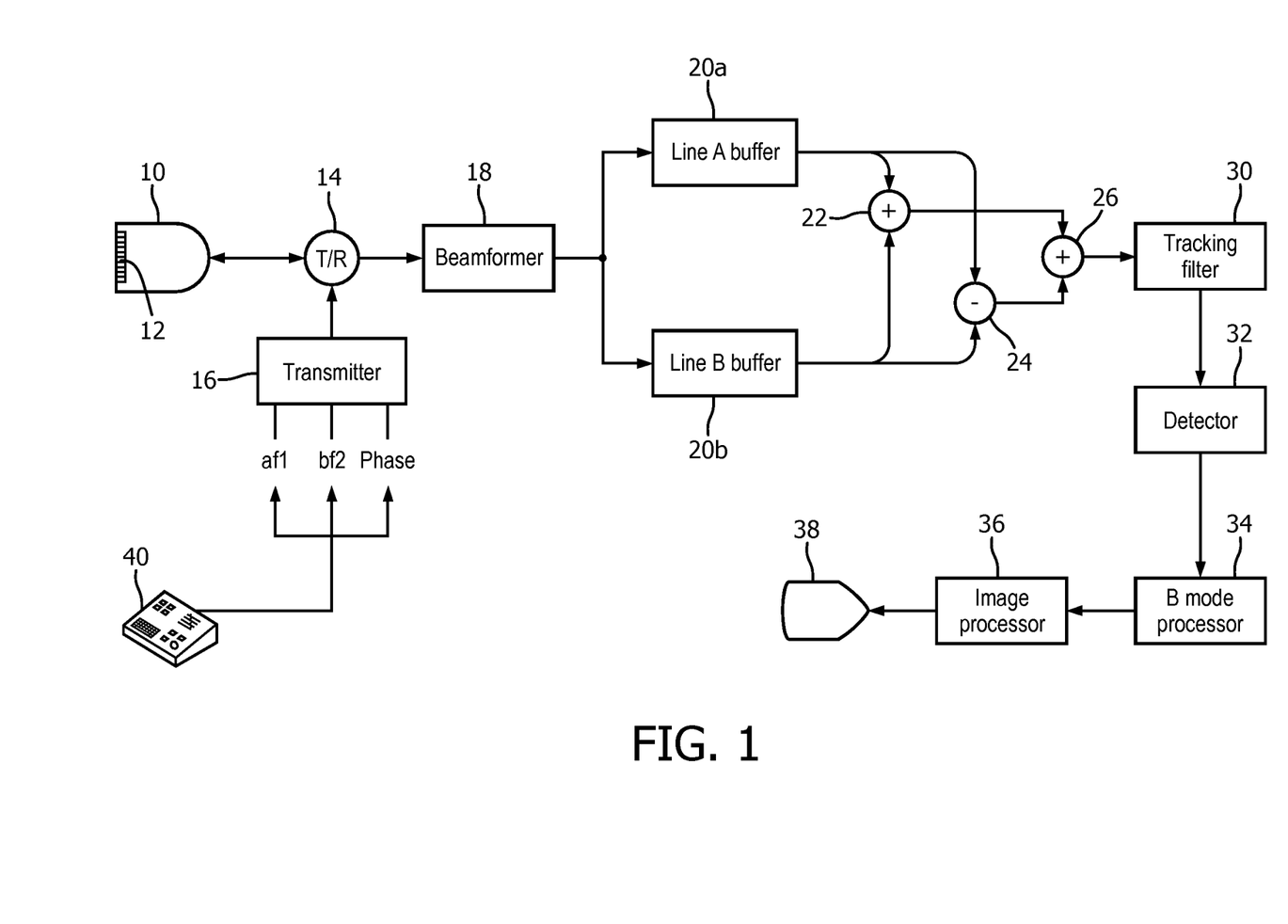
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown. The ultrasound system of FIG. 1 utilizes a transmitter 16 which transmits multi-frequency beams for the nonlinear generation of harmonic and sum and difference frequency signals within the subject being imaged. The transmitter is coupled by a transmit/receive (T/R) switch 14 to the elements of an array transducer 12 of an ultrasound probe 10, which protects the beamformer from high voltage transmit pulses. The transmitter is responsive to a number of control parameters which determine the characteristics of the transmit beams, as shown in the drawing. The two major frequencies $f_1$ and $f_2$ of the multi-frequency transmit beam are controlled, which determine the frequencies at which the sum ($f_1+f_2$) and difference ($f_1-f_2$) frequency components will fall. Also controlled are the amplitudes or intensities a and b of the two transmitted frequency components, causing the transmit beam to be of the form (a sin($2\pi f_1 t$)+b sin($2\pi f_2 t$)). The received sum and difference signal components will have an amplitude c which is not a linear product of the a and b intensities, however, as the sum and difference signals result from the nonlinear effects of intermodulation. Harmonics of the two transmit frequencies are also produced by nonlinear effects.

In FIG. 1, the transducer array 12 receives echoes from the body containing a full spectrum of different frequencies, including the fundamental frequencies $f_1$ and $f_2$, harmonics of these two frequencies, and the sum and difference frequency components which are within the transducer passband. These echo signals are coupled by the T/R switch 14 to a beamformer 18 which appropriately delays echo signals from the different elements then combines them to form a sequence of echo signals along a received beam direction from shallow to deeper depths. Preferably the beamformer is a digital beamformer operating on digitized echo signals to produce a sequence of discrete coherent digital echo signals from a near to a far depth of field. The beamformer may be a multiline beamformer which produces two or more sequences of echo signals along multiple spatially distinct receive scanlines in response to a single transmit beam. The coherent beamformed echoes from along the beam direction are stored in a line A buffer 20a.

Following this first reception of a line of echo signals, a second beam is transmitted in the same beam direction as the first. The transmitter 16 has another variable transmit parameter which is the phase or polarity of the transmit pulse as shown in the drawing. The ultrasound system transmits two or more beams of different transmit polarities, amplitudes and/or phases in the same beam direction. For a two-pulse embodiment, the echoes received in response to the second transmit beam are stored in a line B buffer 20b. The scanline echoes received in response to the two transmit beams are then combined on a spatial (depth) basis in two ways, by addition and subtraction. Alternatively, the second beam of received echoes may be directly combined with the stored echoes of the first beam without buffering.

When the echoes of the two beams are combined by a summer or adder 22, a process known as pulse inversion separation is performed. Pulse inversion separates nonlinear signal components, including the sum, difference, and second harmonic components of the two frequencies of the transmit beams, as described more fully below. As a result of the different phases or polarities of the transmit pulses, the out-of-phase fundamental (linear) echo components will cancel and the nonlinear components, being in-phase, will combine to reinforce each other, producing enhanced and isolated nonlinear harmonic, sum, and difference frequency signals. Nonlinear signal separation can alternatively be performed by power modulated differentiation as described in U.S. Pat. No. 5,577,505 (Brock-Fisher et al.) In accordance with the principles of the present invention the received echoes are also subtractively combined on a spatial basis by a subtractor 24. Subtractive combining cancels the nonlinear components of the two echo signals and reinforces the fundamental linear frequency components from the two echo signals. The results of this subtractive combining process are also described more fully below. The signal components separated by additive and subtractive combining are then combined into a single echo signal at each depth location by a combiner comprising a summer or adder 26.

The echo signals produced by summer or adder 26 are filtered by a filter 30 to remove undesired signals such as out-of-band noise. Preferably the filter 30 is a tracking filter, which varies its passband from high to low frequencies as echo signals are received from increasing depths of field. The tracking filter can be a bandpass filter with a passband that moves from a high frequency band to a low frequency band with increasing depth, or it can be a bandpass filter with a high frequency cutoff that is moved lower in frequency as echoes are received from increasing depths. The depth-dependent tracking filter improves resolution by eliminating high frequencies from further processing when high frequency bands are devoid of useful or uncontaminated signal information due to depth-dependent attenuation.

The filtered echo signals are detected by a detector 32, which may be an amplitude or phase detector. In the illustrated implementation of FIG. 1 the detector is an amplitude detector which detects the envelope of the echo signals, as the echoes are to be processed to form a B mode (grayscale) image. Phase detection is used when the echo signals are to be Doppler processed. The amplitude-detected echo signals are processed by a B mode processor 34 which performs operations such as scan conversion to form grayscale images of tissue in the image field, then further processed for display on an ultrasound image display 38 by an image processor 36

Figure 2:
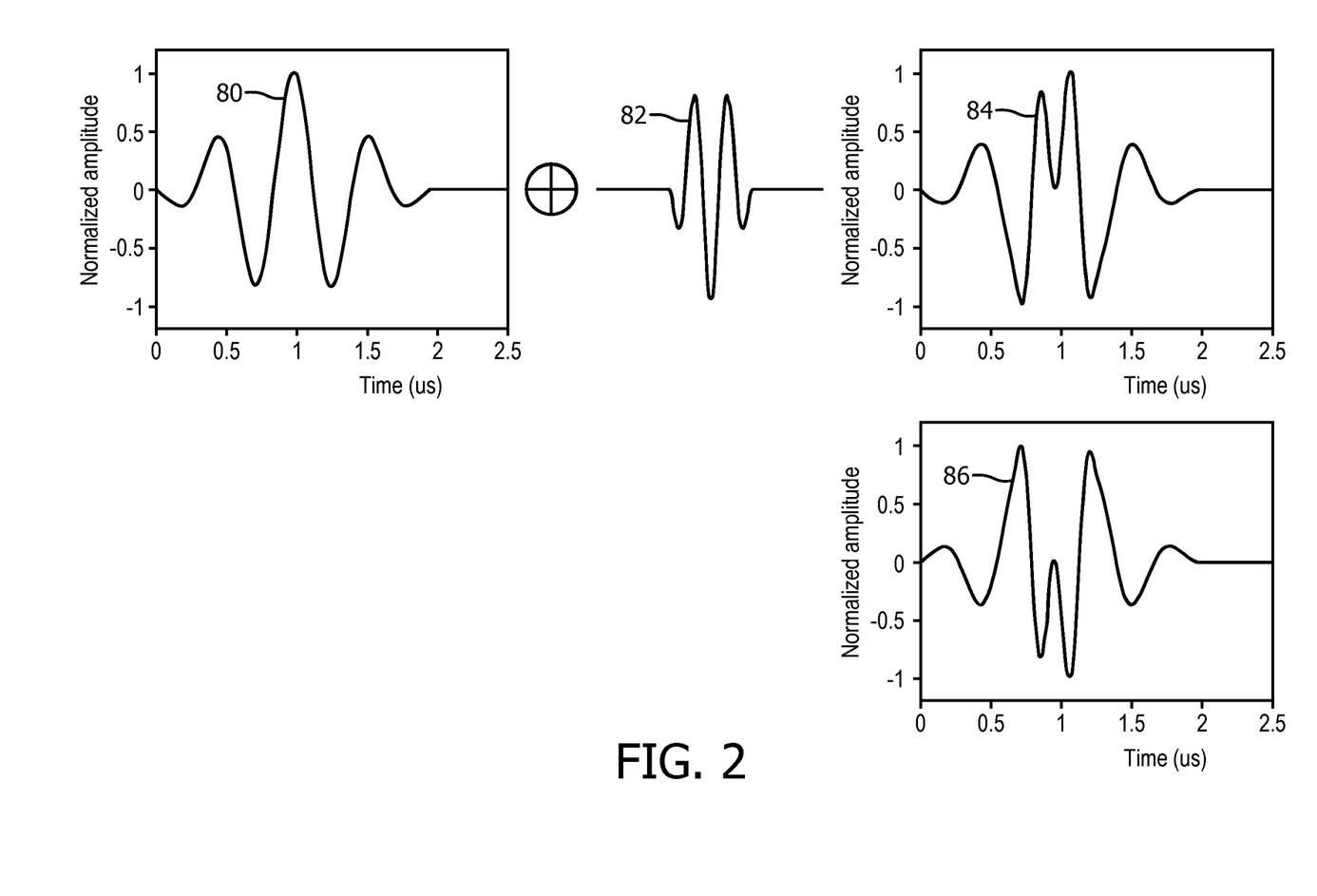
FIG. 2 illustrates the combining of waveforms of different frequencies to produce a multi-frequency transmit waveform and its inverted form.

FIG. 2 illustrates conceptually how the multi-frequency beams transmitted under control of the transmitter 16 are formed. A waveform 80 of a first frequency is combined with a waveform 82 of a second frequency. The multi-frequency combination of these two waveforms is shown as composite waveform 84. A multi-frequency waveform such as waveform 84 is used for the first beam transmitted by the transducer array 12. The waveform 80 is inverted (1800 phase change) to produce a second waveform 86, a phase-inverted replica of the first. The waveform 86 is used for the second beam transmitted by the transducer array in the same beam direction as the first.

Figure 3A:
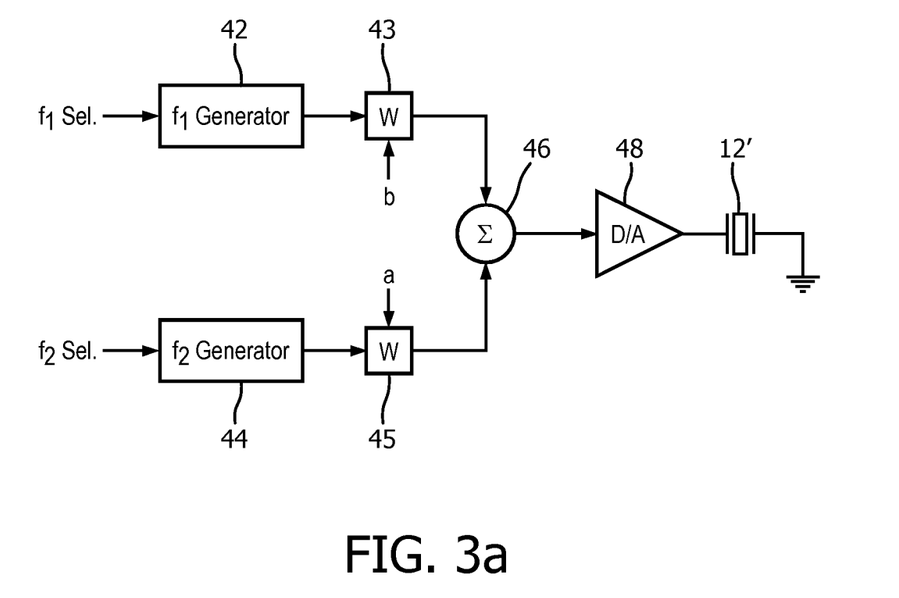
FIGS. 3a and 3b illustrate two ways to produce a multi-frequency transmit waveform in an ultrasound system.

FIGS. 3a and 3b illustrate in detail two implementations of the transmitter 16 suitable for use in an ultrasound system of the present invention. In the implementation of FIG. 3a, the waveforms for the different frequency components $f_1$ and $f_2$ of the transmit pulse are formed separately in digital operations, then combined to form a composite multi-frequency transmit signal for application to a transducer element. An $f_1$ generator 42 produces the $f_1$ transmit signal component and an $f_2$ generator 44 produces the $f_2$ transmit signal component. The generators can generate the signal components algorithmically, for instance. The generators produce their respective transmit waveforms in response to input control parameters such as $f_1$ Sel. and $f_2$ Sel. shown in the drawing which select the $f_1$ and $f_2$ frequency components for the transmit beams. Other variable input parameters (not shown) may be intensity or apodization parameters a and b, and phase or polarity parameters for inverted transmit signals. Alternatively, the output waveforms produced by the generators 42 and 44 may be varied in amplitude and phase or polarity before or after being combined by a summer 46 into a composite transmit waveform which contains the multiple transmit frequency components. In FIG. 3a the waveforms produced by the generators are weighted by digital weighting processor circuits 43 and 45 which apply the amplitude or apodization weighting factors a and b to the generated waveforms. The weighting circuits can take the form of digital multipliers and the sign of the weighting factor (+1,-1) can be used to control the polarity of the output waveform. The composite transmit waveform is applied to a D/A converter 48 for conversion to an analog signal, which may be further amplified and filtered as desired and used to drive a transducer element 12' of the transducer array.

Figure 3B:
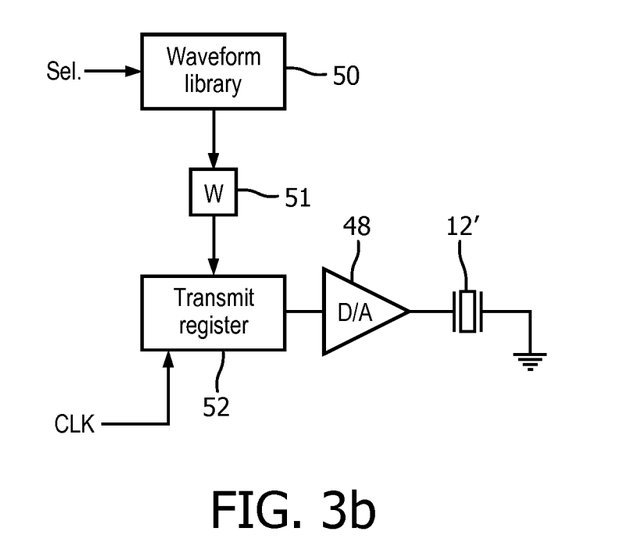

FIG. 3b illustrates a second transmitter implementation in which the composite multi-frequency transmit signals are produced in advance, then stored in a waveform library 50, which may be in the form of a digital memory. When a certain multi-frequency transmit waveform is desired it is selected from the library 50 by a selection signal Sel., weighted by a weighting circuit 51, and stored in a transmit register 52. When the transmitter is triggered to transmit the beam, the composite multi-frequency waveform is shifted out of the transmit register 52 by a clock signal CLK, converted to an analog signal by the D/A converter 48 and applied to the transducer element 12'. The amplitude of the transmit pulse may be varied by either a digital multiplier preceding the A/D converter such as one used in the weighting circuit, or by an analog amplifier following the A/D converter, and may be filtered in either the analog or digital domain as desired. The individual frequency components may not be separately adjusted in amplitude following the transmit register 52 as the waveform is already a composite waveform at that point in this implementation.

Figure 4:
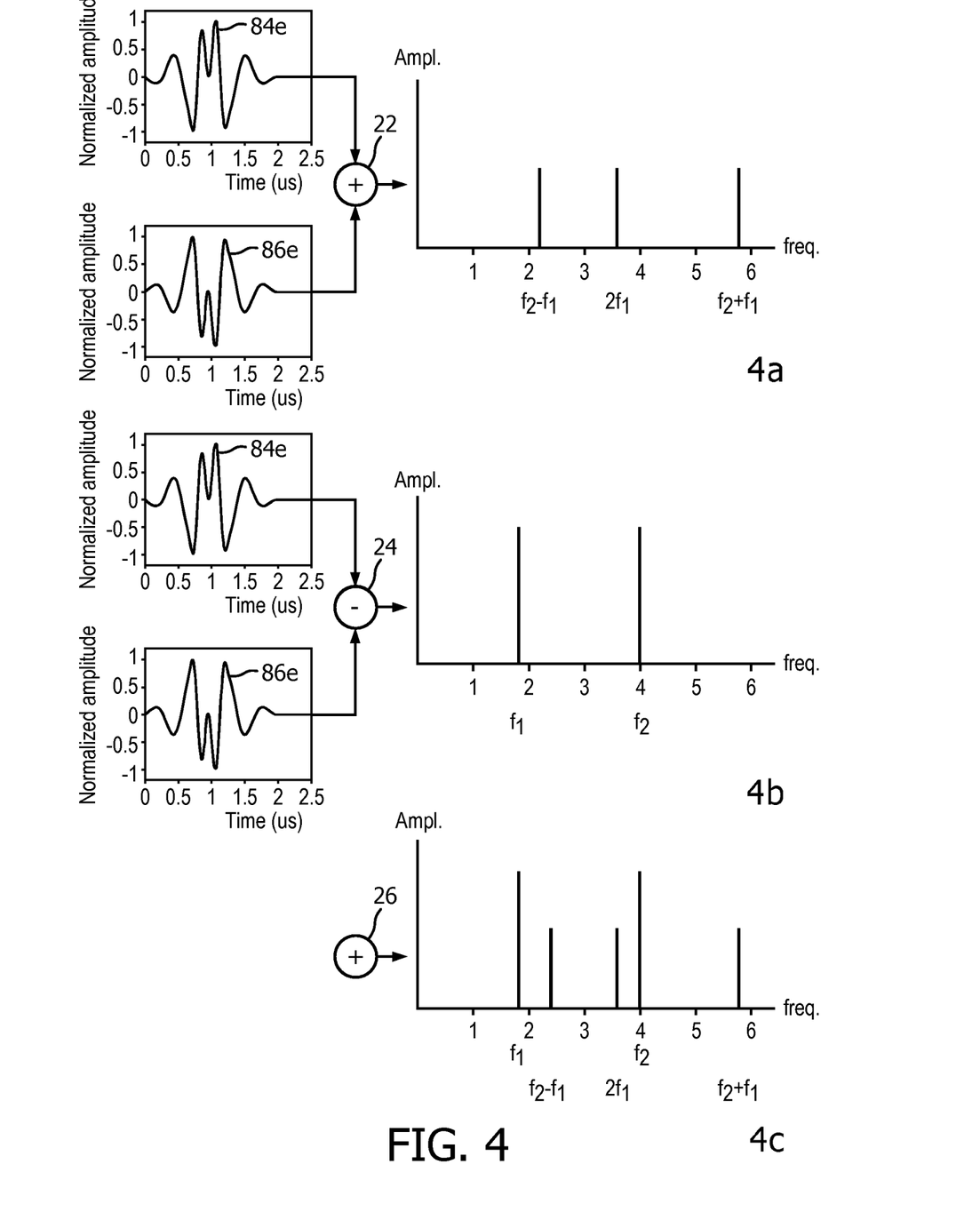
FIG. 4 illustrates different frequency components which may be extracted by adding and subtracting complementary echo signals in accordance with the principles of the present invention.

FIG. 4 illustrates how the ultrasound system acquires a wide spectrum of echo signal frequencies using the transmit waveforms of FIG. 2 for two-pulse transmission at each beam location across the image field. In the top portion 4a of the drawing the ultrasound system additively combines the echo signals 84e and 86e which have been acquired and stored in the two line buffers 20a and 20b. The additive combining by summer 22 separates out the nonlinear difference, second harmonic and sum signal components $f_2-f_1$, $2f_1$, $2f_2$, and $f_2+f_1$, respectively. The summer 22 will also produce a higher frequency second harmonic of the other transmitted frequency component, $2f_2$, which is not shown in the drawing. For the $f_1$ and $f_2$ components selected for transmission in this example, the nonlinear components fall in a transducer passband as shown in the frequency spectrum to the right of summer 22. For clarity of illustration only the center frequencies of the nonlinear component bands are shown in the drawing, although it will be appreciated that each component is actually a band of frequencies around a central frequency. It is seen that the spectrum includes the intermodulation at a high frequency of sum signal components $f_2+f_1$ around 5.8 MHz, a high frequency which produces good near field resolution. These components result from the intermodulation of transmit signal components $f_1$ and $f_2$ in the near field shortly after transmission begins. The middle portion 4b of the drawing shows received echoes 84e and 86e being subtractively combined by subtractor 24, resulting in echo signals of linear fundamental frequency components $f_1$ and $f_2$ as shown to the right of the subtractor. The frequency $f_1$ is a low frequency which is capable of returning at a detectable amplitude in echoes from deeper image depths, with a low frequency withstanding the effect of depth-dependent attenuation. This signal is also a fundamental frequency and thus contains a major portion of the energy reflected from tissue at the greater depths. This signal is further the combination of echoes received in response to both transmissions, and thus, by reason of the subtractive combining, the components from the two echoes reinforce each other to produce a strong received echo from the greater depths. The fundamental frequency echo component $f_2$ is similarly reinforced from both receptions, but is more susceptible to the effect of depth-dependent attenuation. The $f_1$ and $f_2$ frequencies were judiciously chosen in this example so that $f_1$ is the lowest frequency received and capable of acceptable return from the greater depths, while the $f_2$ frequency falls between the nonlinear components $2f_1$ and $f_2+f_1$ of the additive combination.

After the additive and subtractive combinations are combined by the summer 26, the full echo spectrum appears as shown in the bottom portion 4c of the drawing. The spectrum extends from a low frequency of less than 2 MHz in this example to a high frequency of almost 6 MHz. Thus, these echo signals will produce good high frequency resolution in the very near field due to the intermodulated sum frequency component $f_2+f_1$, and good resolution in the far field due to the strong low frequency fundamental signal component $f_1$. A tracking filter 30 (as shown in FIG. 1) which moves from the higher frequencies to the lower frequencies as echoes are processed from the near to the far field will enhance the signal-to-noise performance even more and accentuate the benefits of this wide echo signal spectrum.

Figure 5:
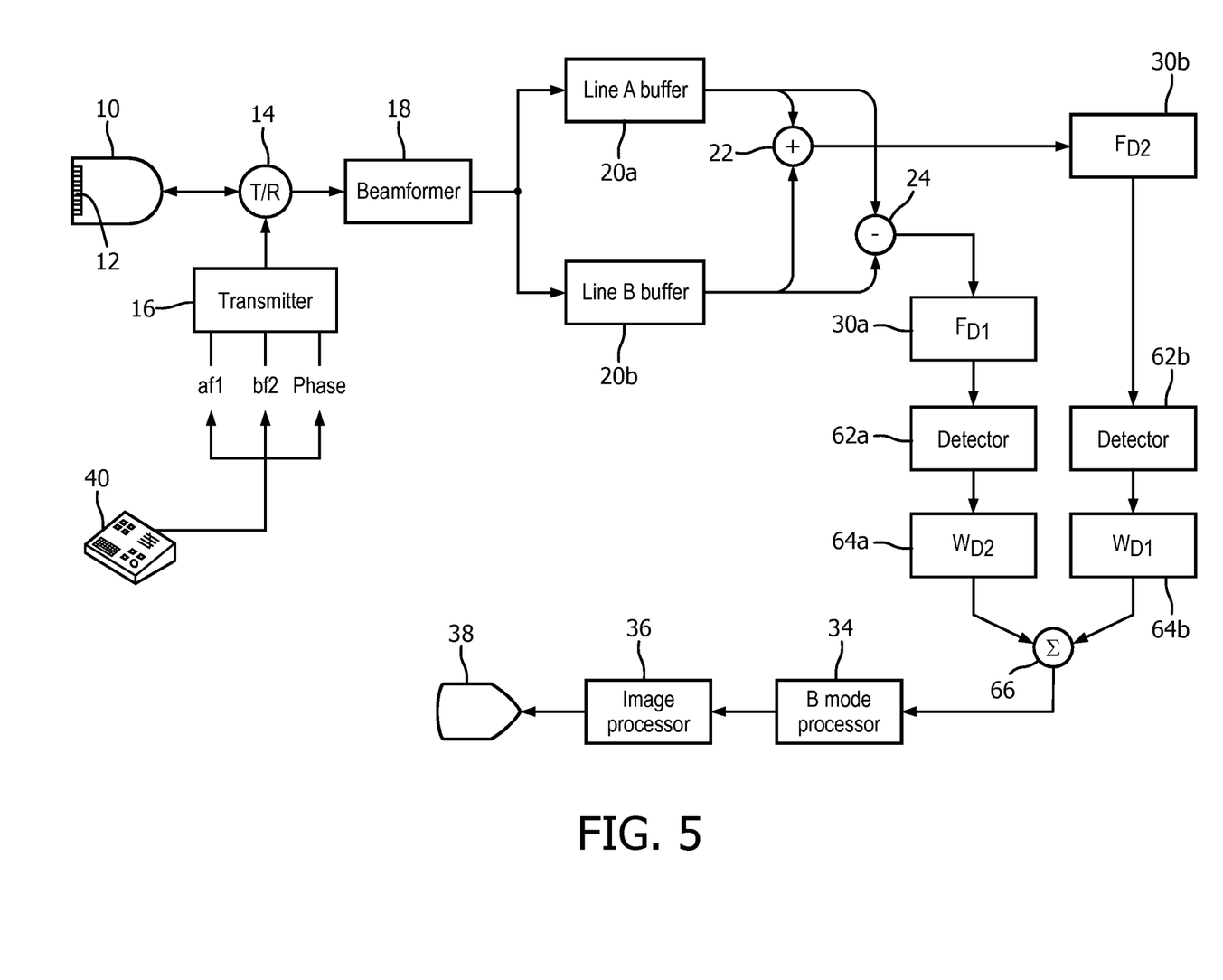
FIG. 5 illustrates an alternative implementation of an ultrasound system of the present invention in block diagram form.

FIG. 5 shows a second implementation of an ultrasound system of the present invention in block diagram form. The system of FIG. 5 is constructed in the same manner as that of FIG. 1 through the additive and subtractive combiners 22 and 24. The outputs of each of these combiners are coupled to two time-varying filters 30a and 30b. These filters exhibit passband characteristics which vary as echo signals are received from increasing depths of field, and provide emphasis of the frequency components which provide the best imaging signals at the respective depths of an image. The filtered linear and nonlinear signals are coupled to detectors 62a and 62b which perform amplitude (envelope) detection of the respective signal components. The detected signals are then weighted by time-varying weighting circuits 64a and 64b, which may be constructed as multiplier circuits, multiplying the applied detected signals by weights which change with time (depth). The weighted signals are then combined by a summing circuit 66. Since the linear signals coming from subtractor 24 and the nonlinear signals coming from adder 22 produce different speckle patterns in an image, an artifact of a coherent signal imaging system, the combining of the two signal paths by the summing circuit 66 will effect a reduction in the combined speckle pattern through a process known as frequency compounding. See U.S. Pat. Re. 35,148 (Lizzi et al.) for a description of the process and effect of frequency compounding for speckle reduction. The combined signals of the summing circuit 66 are then coupled to a B mode processor 34 for image formation and subsequent image processing and display as in the ultrasound system of FIG. 1.

Figure 6A:
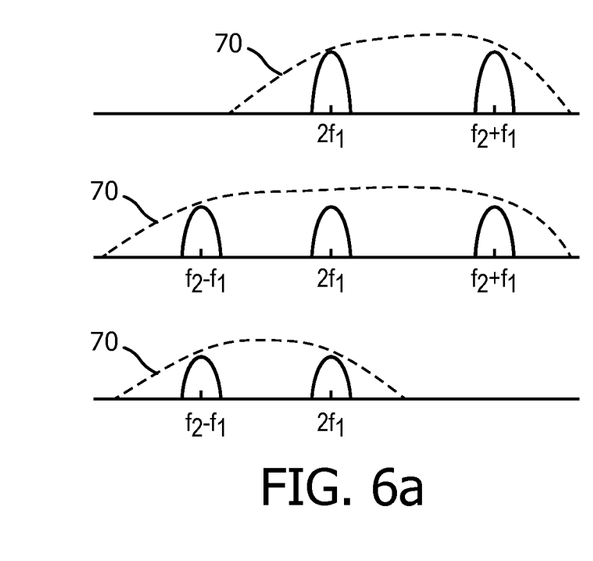
FIG. 6a and FIG. 6b illustrate examples of time-varying passband filter characteristics, according to embodiments of the instant invention.
Figure 6B:
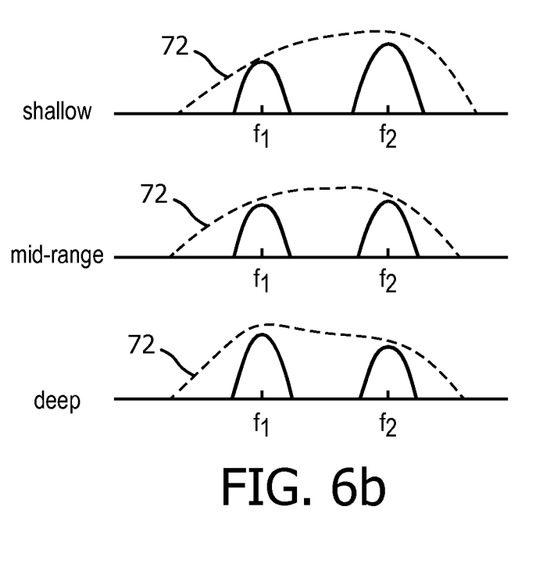

FIGS. 6a and 6b illustrate examples of the time-varying passband characteristics of the filters 30b and 30a, respectively. At a shallow depth the passband 70 of filter 30b is shaped to pass the higher frequency nonlinear components produced by additive combiner 22, which are the intermodulated sum signal components $f_1+f_2$ and the second harmonic components $2f_1$. At shallow depths these higher frequency components are not yet significantly affected by depth-dependent attenuation, and since the higher frequencies produce good resolution, they are preferred for shallow (near field) depths of the image. As echo signals are received from increasing depths, e.g., the mid-range, the filter characteristic 70 transitions to a passband which includes the lower difference frequency components $f_2-f_1$, since these lower frequency nonlinear components are less affected by increasing depth-dependent attenuation than the higher frequency nonlinear components. Nonlinear echo signal components are accentuated in the mid-range of the image. As echo signals are received from greater depths of field (deep), the passband 70 continues to transition to a lower passband which passes the lower nonlinear signal components $f_2-f_1$ and $2f_1$, to the relative exclusion of the highest frequency nonlinear sum signal components. Thus, at each depth the passband 70 is tailored to pass those signals which will produce the best image, in consideration of the good resolution of high frequency signals and the effects of depth-dependent attenuation of high frequencies.

FIG. 6b provides an example of a time-varying filter characteristic 72 which may be used for filter 30a for the linear signal components. At shallow depths the passband of the filter characteristic 72 is greater at the higher frequencies to accentuate the higher fundamental frequencies of the $f_2$ frequency band. This provides higher frequencies with good resolution for the near field region of an image, and the transmitted $f_2$ frequencies will return echo signals from the near field where the nonlinear signals have not yet fully developed, further improving the near field image quality. In the mid-range the filter characteristic 72 becomes more balanced for the passage of both fundamental frequency bands $f_1$ and $f_2$. At the deeper depths the response of the filter characteristic 72 transitions to a lower band to accentuate echoes from the low fundamental frequency signals $f_1$ which are least susceptible to the effects of depth dependent attenuation. Thus, a filter response characteristic such as that shown in FIG. 6b will enhance an image at shallow depths with contributions from $f_2$ frequency echoes, and will enhance the image with good penetration at deeper depths with contributions from echoes of the $f_1$ frequency band.

Figure 7A:
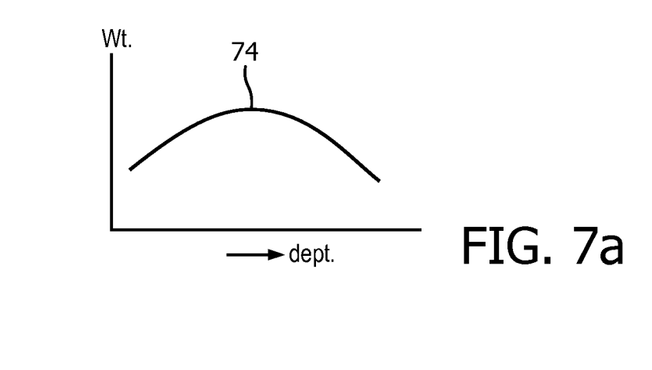
FIG. 7a and FIG. 7b illustrate examples of the variation of weights applied to respective nonlinear and linear echo signal components, according to embodiments of the instant invention.

FIG. 7a provides an example of the variation of weights applied to the nonlinear echo signal components by weighting circuit 64b. The curve 74 shows that the weights are relatively small at the shallowest depth, then progressively increase to greater weighting values in the mid-range. This provides significant contributions from nonlinear echo signals in the mid-range, after nonlinear signal components have had time to develop in the acoustic field and before the effects of depth dependent attenuation have become overly significant. At greater depths the curve 74 shows weights decreasing as the signal to noise ratio of the nonlinear echo signals becomes more greatly affected by depth dependent attenuation.

Figure 7B:
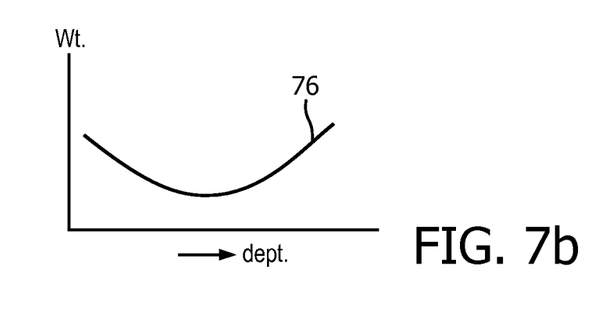

FIG. 7b illustrates an example of the variation of weights applied to the linear echo signal components by weighting circuit 64a. The curve 76 shows greater weights applied in the very near field (shallow depths), increasing the contribution of fundamental frequency echo signals to the image at the shallowest depths where nonlinear signals have not yet significantly developed. The curve 76 decreases (lower weighting) as echoes are received from the mid-range to provide relatively greater contributions from nonlinear echo signals with good resolution. At greater depths the weights increase again as indicated by the rising curve 76, increasing the contribution of lower fundamental frequency echoes with better penetration as the effects of depth dependent attenuation more greatly affect higher frequency nonlinear echo signals.

The values of the weights of the weighting circuit preferably also take into consideration two other factors. One is the need to equalize the relative amplitudes of signals in the linear and nonlinear signal paths for better frequency compounding. When the signals of the two signal paths are appropriately balanced, better reduction of speckle pattern artifacts is achieved. See, in this regard, U.S. Pat. No. 5,957,852 (Hossack et al.) Another is logarithmic compression of the image data. Grayscale values used for a B mode image are conventionally converted to log-varying values, as log conversion has been found to result in a range of grayscale values which are more diagnostically useful. While log conversion can be performed at a variety of points in the image signal path, it is efficient to merge the conversion function into the choice of weights used in the weighting circuits 64a and 64b. Thus, the weighting circuits 64a and 64b can perform three functions: selection of the best combination of linear and nonlinear signal components at different image depths; equalizing the nominal signal amplitudes for effective frequency compounding and speckle reduction; and logarithmic conversion of grayscale image values. Alternatively, log compression may be effected by use of a separate log conversion memory look-up table prior to or following each weighting circuit.

From the above it is seen that the implementation of the concepts of the present invention in the system of FIG. 5 not only enhances image resolution and penetration over the full depth of an image by selective combined use of both linear and nonlinear echo signal components as does the system of FIG. 1, it additionally provides images enhanced by speckle-reduction.

It should be noted that an ultrasound system suitable for use in an implementation of the present invention, and in particular the component structure of the ultrasound system of FIGS. 1, 3a, and 3b, may be implemented in hardware, software or a combination thereof. The various embodiments and/or components of an ultrasound system, for example, the transmitter, the B mode processor, the image processor, the weighting circuits, and the waveform generators, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as the waveform library and the line buffers may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and display of ultrasound images as described above may include various commands that instruct a computer or processor as a processing machine to perform specific operations such as the methods and processes of the various embodiments of the invention, and in particular the adding and subtracting of the received echo signals as described above. The set of instructions may be in the form of a software program. The software may be in various forms such as system software or application software and which may be embodied as a tangible and non-transitory computer readable medium. Further, the software may be in the form of a collection of separate programs or modules such as a beamformer control module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound system for producing high resolution wideband harmonic images comprising:
   an ultrasound probe comprising an array transducer adapted to transmit ultrasound beams and receive echo signals from along directions of transmitted ultrasound beams;
   a transmitter, coupled to the ultrasound probe, and adapted to control the probe to transmit first and second differently modulated transmit waveforms in a common beam direction, each waveform comprising two major frequency components;
   a buffer adapted to store echo signals received in response to transmission of at least the first transmit waveform;
   a summer coupled to the buffer and adapted to additively combine echo signals on a spatial basis which are received in response to transmission of the first and second transmit waveforms;
   a subtractor coupled to the buffer and adapted to subtractively combine echo signals on a spatial basis which are received in response to transmission of the first and second transmit waveforms;
   wherein the summer is further adapted to produce nonlinear echo signal components at an output and the subtractor is further adapted to produce linear echo signal components at an output; and further comprising:
      a first time-varying filter coupled to an output of the summer and adapted to vary from a high pass filter characteristic to a lower band filter characteristic as nonlinear echo signals are received from increasing depths;
      and a second time-varying filter coupled to an output of the subtractor and adapted to vary from a high pass filter characteristic to a lower band filter characteristic as linear echo signals are received from increasing depths;
   and an image processor adapted to produce an ultrasound image, and characterized in that: the summer and the subtractor are further adapted to produce four different major frequency components, each of which is either a fundamental frequency component, a harmonic frequency component, a sum frequency component, or a difference frequency components, and all of which are below the major frequency of the second harmonic component of the transmit waveform of the highest frequency.

2. The ultrasound system of claim 1, wherein the buffer is further adapted to store echo signals received in response to transmission of the second transmit waveform.

3. The ultrasound system of claim 1, wherein the transmitter is further adapted to control the probe to transmit a first waveform, and a second waveform which is an inverted form of the first waveform.

4. The ultrasound system of claim 2, wherein the transmitter is further adapted to control the probe to transmit a first waveform, and a second waveform which is in a 180° phase relationship with the first waveform.

5. The ultrasound system of claim 1, wherein the array transducer is further adapted to receive echo signals which are at fundamental, harmonic, and sum or difference frequencies of the two component frequencies.

6. The ultrasound system of claim 5, wherein the summer is further adapted to produce echo signals of harmonic, sum, and difference frequency components.

7. The ultrasound system of claim 1, wherein the subtractor is further adapted to produce echo signals of fundamental transmit frequency components.

8. The ultrasound system of claim 7, further comprising a combiner, coupled to the summer and the subtractor, and adapted to produce echo signals of fundamental, harmonic, and sum or difference frequency components.

9. The ultrasound system of claim 8, further comprising a tracking filter coupled to the combiner and the image processor.

10. The ultrasound system of claim 1, wherein the second time-varying filter is further adapted to accentuate the contributions of high frequency linear echo signals to an image at a shallow depth and to accentuate the contributions of low frequency linear echo signals to the image at a deeper depth.

11. The ultrasound system of claim 10, wherein the first time-varying filter is further adapted to accentuate the contributions of nonlinear echo signals to the image in the mid-range.

12. The ultrasound system of claim 1, further comprising:
    a first detector coupled to an output of the first time-varying filter;
    a second detector coupled to an output of the second time-varying filter;
    and a summing circuit coupled to outputs of the first and second detectors,
    wherein the summing circuit is adapted to produce speckle-reduced echo signals.

13. The ultrasound system of claim 12, further comprising:
    a first weighting circuit coupled between the first detector and the summing circuit and adapted to apply weights which vary as a function of depth to nonlinear echo signals; and
    a second weighting circuit coupled between the second detector and the summing circuit and adapted to apply weights which vary as a function of depth to linear echo signals.

14. The ultrasound system of claim 13, wherein the first weighting circuit is further adapted to apply the greatest weights to echo signals at mid-range depths of field; and
    wherein the second weighting circuit is further adapted to apply the greatest weights to echo signals at shallow and deeper depths of field.

* * * * *